United States Patent

Mewshaw

[11] Patent Number: 5,684,039
[45] Date of Patent: Nov. 4, 1997

[54] CHROMAN-2-YLMETHYLAMINO DERIVATIVES

[75] Inventor: Richard E. Mewshaw, South Brunswick, N.J.

[73] Assignee: American Home Products Corporation, Madison, N.J.

[21] Appl. No.: 684,610

[22] Filed: Jul. 19, 1996

Related U.S. Application Data

[60] Provisional application No. 60/001,422, Jul. 25, 1995.

[51] Int. Cl.[6] ..................... A61K 31/35; C07D 311/58
[52] U.S. Cl. ............................. 514/456; 549/407
[58] Field of Search ........................ 549/407; 514/456

[56] References Cited

U.S. PATENT DOCUMENTS

| | | |
|---|---|---|
| 4,321,270 | 3/1982 | Sundeen . |
| 5,126,367 | 6/1992 | Stack et al. . |
| 5,137,901 | 8/1992 | Junge et al. . |
| 5,318,988 | 6/1994 | Schohe-Loop et al. . |
| 5,371,094 | 12/1994 | Heine et al. . |

FOREIGN PATENT DOCUMENTS

| | | |
|---|---|---|
| 0325964 | 8/1989 | European Pat. Off. . |
| 0334429 | 9/1989 | European Pat. Off. . |
| 0369874 | 5/1990 | European Pat. Off. . |
| 9505383 | 2/1995 | WIPO . |

OTHER PUBLICATIONS

Indian Journal of Chemistry, 20B, 12, 1063–1067, Dec. 1981.

*Primary Examiner*—Nicky Chan
*Attorney, Agent, or Firm*—Richard K. Jackson

[57] ABSTRACT

Compounds of the formula:

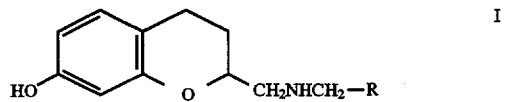

in which R is a straight or branched chain alkyl group of 1 to 6 carbon atoms, hydroxyalkyl of 1 to 6 carbon atoms or a cycloalkyl group of 3 to 8 carbon atoms; or a pharmaceutically acceptable salt thereof are inhibitors of dopamine synthesis and release, useful in the treatment of schizophrenia, Parkinson's Disease, Tourette's Syndrome, alcohol addiction, cocaine addiction, and addiction to analagous drugs.

12 Claims, No Drawings

CHROMAN-2-YLMETHYLAMINO DERIVATIVES

BACKGROUND OF INVENTION

This application claims the benefit of U.S. Provisional aspplication Ser. No. 60/001,422, filed Jul. 25, 1995.

Efforts to induce antipsychotic activity with dopamine autoreceptor agonists have been successful (Corsini et al. Adv. Biochem. Psychopharmacol 16, 645–648, 1977; Tamminga et at. Science 200, 567–568, 1978; and Tamminga et al. Psychiatry 398–402, 1986). A method for determining intrinsic activity at the dopamine $D_2$ receptor was recently reported [Lahti et al., Mol. Pharm. 42, 432–438, (1993)]. Intrinsic activity is predicted using the ratio of the "low-affinity agonist" (LowAg) state of the receptor and the "high-affinity agonist" (HighAg) state of the receptor, i.e. LowAg/HighAg. These ratios correlate with the agonist, partial agonist, and antagonist activities of a given compound, which activities characterize a compounds ability to elicit an antipsychotic effect.

EP 0 369 874 discloses some 6-hydroxy-2-methyl-2-dialkylaminoalkyl-benzopyran derivatives as cardioprotective agents U.S. Pat. No. 4,321,270 discloses a group of benzopyrans which may contain an alkylaminoalkyl substituent in 2-position as antiinflamatory agents.

DESCRIPTION OF THE INVENTION

In accordance with this invention, there is provided a group of compounds which are useful antipsychotic agents. The compounds of this invention are essentially free from extrapyramidal side effects (EPS). The compounds of this invention are selective autoreceptor agonists, functioning primarily to activate only autoreceptors versus postsynaptic $D_2$ dopamine receptors). As such, they provide functional modulation of dopamine systems of the brain without the excessive blockade of the postsynaptic dopamine receptors, which have been observed to be responsible for the serious side effects frequently exhibited by agents found otherwise clinically effective for treatment of schizophrenia. Activation of the dopamine autoreceptors results in reduced neuronal firing a well as inhibition of dopamine synthesis and release and therefore provide a means of controlling hyperactivity of the dopaminergic systems.

More specifically, the compounds of this invention are depicted by the following Formula I:

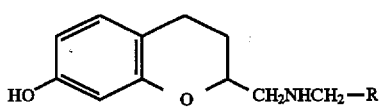

in which
R is a straight or branched chain alkyl group of 1 to 6 carbon atoms, hydroxyalkyl of 1 to 6 carbon atoms or a cycloalkyl group of 3 to 8 carbon atoms; or a pharmaceutically acceptable salt thereof.

The pharmaceutically acceptable salts are those derived from such organic and inorganic acids as: acetic, lactic, citric, fumaric, tartaric, succinic, maleic, malonic, oxalic, hydrochloric, hydrobromic, phosphoric, nitric, sulfuric, methanesulfonic, methylbenzene sulfonic, and similarly known acceptable acids. The compounds of this invention contain an asymmetric carbon atom and therefore appear as racemic mixtures which are readily resolved into their pure enantiomers by conventional means.

The compounds of Formula I are prepared by the overall sequence as follows:

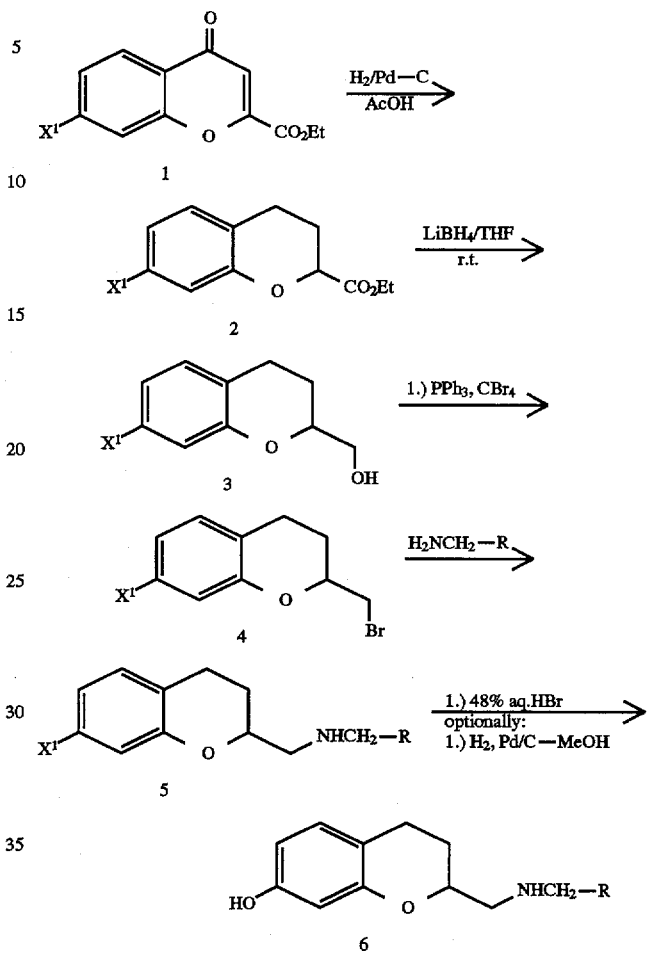

In this reaction sequence, $X^1$ is protected oxygen in which the protecting group is methyl, benzyl, and the like, known oxygen protecting groups. The final step of the reaction sequence, from compound 5 to 6, involves deprotection of oxygen to provide the hydroxy group in 7-position of the benzopyran ring.

Specific exemplification of the production of representative compounds of this invention is given in the following procedures:

INTERMEDIATE 1

Ethyl (R,S)-3,4-Dihydro-7-methoxy-2H-1-benzopyran-2-carboxylate

A solution of ethyl 7-methoxy-4-oxo-4H-1-benzopyran-2-carboxylate [prepared from 1-hydroxy-5-methoxy-acetophenone according to Appleton et al. J. Med. Chem.20, 371–379, (1989)] in acetic acid (200 mL) was hydrogenated over 10% palladium on carbon at room temperature at 50 psi for 5 days. The reaction mixture was filtered through celite and the solvent was removed under vacuum. The product crystallized and was then triturated with 1:1 ethyl acetate-hexane to afford 20 g (72% yield) of product, mp 63°–64° C.; MS (EI) m/e 236 (M+).

Elemental Analysis for $C_{13}H_{16}O_4$ Calc'd: C, 66.09; H, 6.83 Found: C, 65.65; H, 6.76

INTERMEDIATE 2

(R,S)-3,4-Dihydro-7-methoxy-2H-1-benzopyran-2-methanol (R,S)-3,4-Dihydro-7-methoxy-2H-1-benzopyran-2-carboxylic acid ethyl ester (20 g) was dissolved in tetrahydrofuran (215 mL) and a 2.0M solution of lithium borohydride (100 mL, 0.20 moles) was added over 0.5 hour. After two hours the reaction was complete and the excess lithium borohydride was destroyed by the cautious addition of methanol. The reaction mixture was then diluted with ethyl acetate and washed with water. The organic layer separated and dried under vacuum to afford 16 g (96% yield) of a clear oil: IR (CDCl$_3$) 3600, 3450, 2920, 1620, 1585, and 1510 cm$^{-1}$; MS (EI) m/e, 194 (M+); $^1$H NMR (CDCl$_3$) δ 1.75–1.94 (2H, m), 2.08 (1H, bs), 2.67–2.84 (2H, m), 3.74–3.86 (2H, m), 3.76 (3H, s), 4.09 (1H, m), 6.40 (1H, d, J=2.6 Hz), 6.46 (1H, dd, J=8.35, 2.64 Hz), 6.94 (1H, d, J=8.35 Hz).

INTERMEDIATE 3

(R,S)-3,4-Dihydro-7-(phenylmethoxy)-2H-1-benzopyran-2-methanol

To a solution of (R,S)-3,4-dihydro-7-(phenylmethoxy)-2H-1-benzopyran-2-carboxylic ethyl ester [(86.1 g, 0.27 mol) prepared as reported in J. Med. Chem. 1989, 32, 1842–1860] in 800 mL of tetrahydrofuran was added dropwise at 0° C. a 2.0M solution of lithium borohydride in tetrahydrofuran (2.4 eq). The reaction was allowed to stir for 18 hours at room temperature then the excess lithium borohydride was destroyed by the cautious addition of water. The solvent was removed under vacuum and the residue dissolved in ethyl acetate (1 L) and washed with water (200 mL). The organic layer separated and dried over anhydrous magnesium sulfate, filtered, and the solvent removed under vacuum to afford 71.5 g (98%) of a light yellow oil: MS (EI) m/z 270 (M+); $^1$H NMR (DMSO-d$_6$) δ 1.57–1.67 (1H, m), 1.92–1.98 (1H, m), 2.48–2.73 (2H, m), 3.51–3.61 (2H, m), 4.74 (1H, t, J=5.71 Hz), 5.02 (2H, s), 6.36 (1H, d, J=2.64), 6.46 (1H, dd, J=8.35, 2.64 Hz), 6.92 (1H, d, J=8.35 hz), 7.28–7.41 (5H, m).

INTERMEDIATE 4

(R,S)-3,4-Dihydro-7-methoxy-2H-1-benzopyran-2-methylbromide

To a solution of (R,S)-3,4-dihydro-7-methoxy-2H-1-benzopyran-2-methanol (3.14 g, 16.2 mmol) and carbontetrabromide (9.13g, 28 mmol) in methylene chloride (50 ml) was slowly added a solution of triphenylphosphine (7.21g, 27.5 mmol) in methylene chloride (50 mL) at 0° C. The reaction was allowed to warm to room temperature and stirred for 12 hours, then poured into water (150 mL) and extracted with methylene chloride (300 mL), dried and the solvent evaporated. Purification by chromatography (15% ethyl acetate/hexanes) afforded 3.16 g (75% yield) of a clear oil: IR (film) 2920, 1620, 1580, 1505, 1440, and 1160 cm−1; MS (EI) m/e, 258 (M+), 256 (M+); $^1$H NMR (CDCl$_3$) δ 1.84–1.93 (1H, m), 2.11–2.18 (1H, m), 2.72–2.80 (2H, m), 3.52 (1H, dd, J=10.54, 5.93 Hz), 3.59 (1H, dd, J=10.54, 5,49 Hz), 3.75 (3H, s), 4.18–4.24 (1H, m), 6.40 (1H, d, J=2.42 Hz), 6.45 (1H, dd, J=8.35, 2.64 Hz), 6.94 (1H, d, J=8.35 Hz).

INTERMEDIATE 5

(R,S)-3,4-Dihydro-7-(benzyloxy)-2H-1-benzopyran-2-methylbromide

To a solution of (R,S)-3,4-dihydro-7-(phenylmethoxy)-2H-1-benzopyran-2-methanol (76.0 g, 0.28 mol) and carbontetrabromide (152.6 g, 0.46 mol) in methylene chloride (800 mL) was slowly added a solution of triphenylphosphine (120.6 g, 0.46 mol) in methylene chloride (400 mL) at 0° C. The reaction was allowed to stir for 12 hours at room temperature and the solvent concentrated under vacuum. The oily residue was dissolved in a minimum amount of methylene chloride (300 mL) and allowed to stand for 1 hour. The solids were then filtered and the solvent again removed. The residue was chromatographed (5% ethyl acetate-petroleuum ether) to afford 42.2 g (45.2%) of the title compound as a white solid: mp 76°–78° C.

Elemental analysis for C$_{17}$H$_{17}$BrO$_2$ Calc'd: C, 61.28; H, 5.14. Found: C, 61.26; H, 5.04.

INTERMEDIATE 6

1-(7-Methoxy-chroman-2-ylmethyl-amino)-propane

A mixture of 3,4-dihydro-7-methoxy-2H-1-benzopyran-2-methylbromide (2.0 g, 7.7 mmol) and 1-aminopropane (10 eq) were heated to reflux for 18 hrs. The reaction mixture was poured into water (150 mL) and extracted with methylene chloride (3×150 ml). The organic layer was dried and the solvent evaporated to afford 1.81 g of desired product (100%): IR (film) 2960, 1620, 1580, 1505, 1380, and 1160 cm−1; MS m/e, 235 (M+).

This general procedure utilizing n-butylamine, isobutylamine, n-pentylamine, 3-methylbutylamine afforded:

Butyl-(7-methoxy-chroman-2-ylmethyl)-amine oxalate salt, mp 210°–212° C., (99%)

Elemental analysis for C$_{15}$H$_{23}$NO$_2$.C$_2$H$_2$O$_4$ Calc'd: C, 60.16; H, 7.42; N, 4.13 Found: C, 59.95; H, 7.50: N, 3.99
Isobutyl-(7-methoxy-chroman-2-ylmethyl)-amine, (91%); IR (film) 2950, 1620, 1600, 1505, 1405 and 1390 cm$^{-1}$; MS m/e, 249 (M+)
Pentyl-(7-methoxy-chroman-2-ylmethyl)-amine, (91%): IR ((film) 2900, 1630, 1600, 1503, and 1405 cm−1; MS m/e 263 (M+).

3-Methyl-butyl-1-(7-methoxy-chroman-2-ylmethyl)-amine oxalate salt (1:1 ) quarter hydrate, mp 221°–222° C. (97%)

Elemental analysis for C$_{16}$H$_{25}$NO$_2$.C$_2$H$_2$O$_4$.0.25H$_2$O Calc'd: C, 60.40; H, 7.74; N, 3.91 Found: C, 60.53, H, 7.65: N, 3.80

INTERMEDIATE 7

3-[(7-Benzyloxychroman-2-ylmethyl)-amino]-pronan-1-ol

A mixture of (R,S)-3,4-dihydro-7-(benzyloxy)-2H-1-benzopyran-2-methylbromide (42.1 g, 0.13 mol) and 100 mL of 1-amino-3-propanol (10 eq) were heated to 100° C. for 2 hours. The reaction mixture was poured into 2.5 L of water and extracted with ethyl acetate (4×1 L). The organic layer was dried over anhydrous magnesium sulfate, filtered, and the solvent evaporated to afford 41.8 g (98%). of a pale yellow solid: mp 54°–55° C.; MS (EI) m/e 327 (M+).

Elemental analysis for C$_{20}$H$_{25}$NO$_3$ Calc'd: C, 73.37; H, 7.70; N 4.28 Found: C, 73.85; H, 7.84; N, 4.34.

INTERMEDIATE 8

[7-(Benzyloxy-chroman-2-ylmethyl)-amino]-1-methylethane

A mixture of 3,4-dihydro-7-(benzyloxy)-2H-1-benzopyran-2-methylbromide (2.0 g, 6.0 mmol) and isopropylamine (10 eq) were heated to reflux for 3 days. The reaction mixture was concentrated under high vacuum and the residue was chromatographed (5% methanol-methylene chloride) to afford 1.44 g (77.0%) of product as a thick oil: IR (KBr) 2950, 1620, 1560, 1500 and 1400 cm–1; MS m/e, 311 (M+)

This general procedure utilizing cyclohexylamine, 1-ethyl-propylamine, dipropyl-amine, n-hexylamine and cyclohexylmethylamine afforded:

[(7-Benzyloxy-chroman-2-ylmethyl)-amino]-cyclohexane (87%); IR (KBr) 3400, 2900, 1600, 1550, 1505, and 1400 cm–1; MS m/e, 261 (M+)

1-[(7-Benzyloxy-chroman-2-ylmethyl)-amino]-1-ethyl-propane, (60%); MS m/e, 339 (M+)

1-[(7-Benzyloxy-chroman-2-ylmethyl)-(propyl)-amino]-propane, (81%): MS m/e, 353 (M+)

1-[(7-Benzyloxy-chroman-2-ylmethyl)-amino]-hexane (100%): IR (film) 2900, 1650, 1600, 1502, and 1400 cm–1; MS m/e 353 (M+).

(7-Benzyloxy-chroman-2-ylmethyl)-(cyclohexylmethyl)-amine oxalate salt, (98%); IR (film) 1650, 1580, 1500 cm–1; MS FAB 366 (M+H).

EXAMPLE 1

2-Butylaminomethyl-chroman-7-ol

A solution of butyl-(7-methoxy-chroman-2-ylmethyl)-amine (1.15 g, 4.6 mmol) in 48% aqueous HBr (40 mL) was heated to reflux for 3 hours. The reaction mixture was then allowed to cool to room temperature and basified with 1N NaOH until pH 12. The basic reaction mixture was extracted with ethyl acetate (3×100 mL), dried and the solvent removed under vacuum. Chromatography (10% MeOH/ $CH_2Cl_2$) afforded 597 mg (55%) of product. The corresponding oxalate salt was prepared, mp 175°–178° C.

Elemental analysis for $C_{14}H_{21}NO_2 \cdot C_2H_2O_4 \cdot 0.25H_2O$ Calc'd: C, 59.07; H, 7.13; N, 4.31 Found: C, 57.28; H, 6.94; N, 3.99

This general demethylation procedure also afforded:

(1b) 2-(Propylaminomethyl)-chroman-7-ol oxalate salt (2:1), mp 216°–219° C.

Elemental analysis for $C_{13}H_{19}NO_2 \cdot 0.5(COOH)_2$ Calc'd: C, 63.14; H, 7.57; N, 5.26 Found: C, 62.82; H, 7.59; N, 5.01

(1c) 2-(Isobutylaminomethyl)-chroman-7-ol oxalate salt, mp 158°–160° C.

Elemental analysis for $C_{14}H_{21}NO_2 \cdot (COOH)_2$ Calc'd: C, 59.06; H, 7.12; N, 4.31 Found: C, 58.66; H, 7.18; N, 4.20

(1d) 2-[(3-Methyl-butylamino)-methyl]-chroman-7-ol oxalate salt, mp 185°–186° C.

Elemental analysis for $C_{15}H_{23}NO_2 \cdot (COOH)_2$ Calc'd: C, 60.16; H, 7.43; N, 4.31 Found: C, 59.76; H, 7.39; N, 4.17

(1e) 2-(Pentylaminomethyl)-chroman-7-ol oxalate salt, mp 169°–170° C.

Elemental analysis for $C_{15}H_{23}NO_2 \cdot (COOH)_2$ Calc'd: C, 60.16; H, 7.43; N, 4.31 Found: C, 59.82; H, 7.43; N, 4.44

EXAMPLE 2

2-(Hexylaminomethyl)-chroman-7-ol

A solution of 1-[7-(benzyloxy-chroman-2-ylmethyl)-amino]-1-hexane (2.55 g, 7.2 mmol) in methanol (120 mL) containing 10% palladium on carbon (300 mg) was hydrogenated at 50 psi for 18 hours. The mixture was filtered through Celite®, washed with methanol, and the solvent evaporated. Chromatography (silica, 2% methanol in methylene chloride) afforded 1.53 g (81%) of a white solid. The free base was dissolved in isopropanol (20 mL) and a solution of oxalic acid (3 eq) in methanol (15 mL) was added. Upon cooling to room temperature an off-white solid precipitated and was filtered to afford 1.13 g of the title a compound as the oxalate salt, mp 171°–173° C.

Elemental analysis for $C_{16}H_{25}NO_2 \cdot (COOH)_2$ Calc'd: C, 61.17; H, 7.70; N, 3.96 Found: C, 60.85; H, 7.77; N, 4.05

This general hydrogenolysis procedure was used to afford:

(2b) 2-{(3-Hydroxy-propylamino)-methyl]-chroman-7-ol oxalate salt (1:1), mp 163°–165° C., (71.2%).

Elemental analysis for $C_{13}H_{19}NO_3 \cdot (COOH)_2$ Calc'd: C, 55.04; H, 6.47; N, 4.28 Found: C, 54.64; H, 6.48; N, 4.20

(2c) 2-(Isopropylamino-methyl]-chroman-7-ol oxalate salt (1:1), mp 195°–196° C.

Elemental analysis for $C_{13}H_{19}NO_2 \cdot (COOH)_2$ Calc'd: C, 58.87; H, 6.80; N, 4.50 Found: C, 57.66; H, 6.82; N, 4.39

(2d) 2-(Cyclohexylaminomethyl)-chroman-7-ol oxalate salt (1:1), mp 190°–191° C.

Elemental analysis for $C_{16}H_{22}NO_2 \cdot (COOH)_2$ Calc'd: C, 61.70; H, 6.90; N, 4.00 Found: C, 62.07; H, 7.30; N, 3.99

(2e) 2-(Dipropylaminomethyl)-chroman-7-ol oxalate salt quarter hydrate, (2:1), mp 205°–206° C.

Elemental analysis for $C_{16}H_{25}NO_2 \cdot 0.5(COOH)_2 \cdot 0.25H_2O$ Calc'd: C, 65.25; H, 8.54; N, 4.32 Found: C, 65.41; H, 8.54; N, 4.32

(2f) 2-[(1-Ethyl-propylamino)-methyl]-chroman-7-ol oxalate salt (2:1) hydrate (2:1), mp 165°–166° C.

Elemental analysis for $C_{15}H_{23}NO_2 \cdot 0.5(COOH)_2 \cdot OH_2 \cdot 1.0H$ Calc'd: C, 61.17; H, 7.70; N, 3.96 Found: C, 60.85; H, 7.77; N, 4.05

(2g) 2-[(Cyclohexylmethyl-amino)-methyl]-chroman-7-ol oxalate salt (1:1), mp 160°–161° C.

Elemental analysis for $C_{17}H_{25}NO_2 \cdot C_2H_2O_4$ Calc'd: C, 62.45; H, 7.45; N, 3.83 Found: C, 62.16; H, 7.51; N, 3.82

The compounds of this invention are dopamine autoreceptor agonists, that is, they serve to modulate the synthesis and release of the neurotransmitter dopamine. They are thus useful for treatment of disorders of the dopaminergic system, such as schizophrenia, Parkinson's disease and Tourette's syndrome. Such agents are partial agonists at the postsynaptic dopamine $D_2$ receptor and are thereby useful in the treatment of alcohol and drug addiction.

Affinity for the dopamine autoreceptor was established by a modification of the standard experimental test procedure of Seemen and Schaus, European Journal of Pharmacology 203: 105–109, 1991, wherein homogenized rat striatal brain tissue is incubated with $^3$H-quinpirole (Quin.) and various concentrations of test compound, filtered and washed and counted in a Betaplate scintillation counter.

High affinity for the dopamine D-2 receptor was established by the standard experimental test procedure of Fields, et al., Brain Res., 136, 578 (1977) and Yamamura et al., eds., Neurotransmitter Receptor Binding, Raven Press, New York (1978) wherein homogenized limbic brain tissue is incubated with $^3$H-spiroperidol (Spiper.) and various concentrations of test compound, filtered and washed and shaken with Hydrofluor scintillation cocktail (National Diagnostics) and counted in a Packard 460 CD scintillation counter.

The results of the tests with compounds representative of this invention and some very similar analogues are given in the immediately following table. From the agonist activity of these compounds, presented in column 1 (Quin.), it can be seen that compounds having the 7-hydroxy substituent are markedly more potent than the 7-methoxy substituted compounds although these two substituents are generally considered to be equivalents in the prior art. In addition, it can be seen that two alkyl substituents on the amino group reduces potency dramatically. And, branched chain alkyl or cycloalkyl groups directly substituted on the amino group markedly reduce potency.

| Structure | IC$_{50}$ (nM) Quin. | IC$_{50}$ (nM) Spiiper. | IC50 (nM) 5HT1a | IC50 (nM) $\alpha_1$ | Ratio Ant/Ag |
|---|---|---|---|---|---|
| 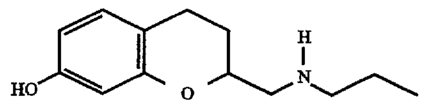 | 10.8 | 1274 | 354 | 1163 | 118 |
| 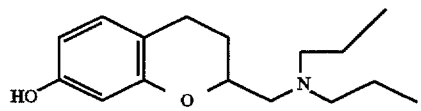 | 102 | 8,960 | — | — | 88 |
| 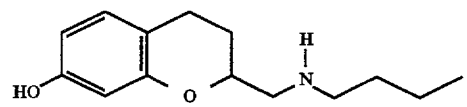 | 6.1 | 1173 | 537 | 354 | 192 |
| 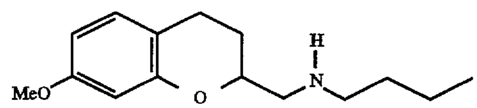 | 733 | 23587 | — | — | 32 |
| 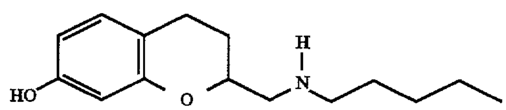 | 1.84 | 590 | 26 | 320 | 320 |
| 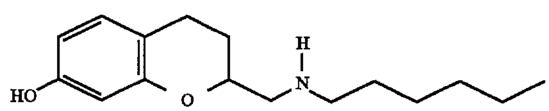 | 1.63 | 313 | 5.76 | 221 | 192 |
| 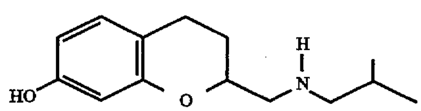 | 15.85 | 1493 | 617 | 90.3 | 94 |
| 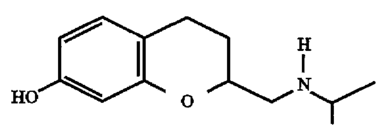 | 103 | — | — | — | — |
| 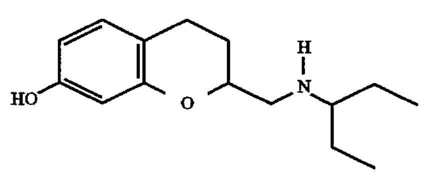 | 111 | 7459 | — | — | 67 |
| 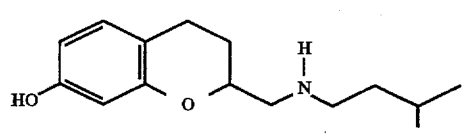 | 3.07 | 477 | 134 | 750 | 155 |
| 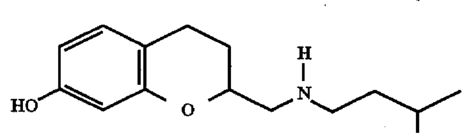 | 831 | 26470 | — | — | 32 |

| Structure | IC$_{50}$ (nM) Quin. | IC$_{50}$ (nM) | IC50 (nM) 5HT1a | IC50 (nM) $\alpha_1$ | Ratio Ant/Ag |
|---|---|---|---|---|---|
| (structure 1) | 1.82 | 113 | 53 | 829 | 62 |
| (structure 2) | 49 | 4,622 | — | — | 94 |
| (structure 3) | 6.72 | 2850 | 172 | 614 | 424 |
| (structure 4) | 2413 | >30000 | — | — | — |
| (structure 5) | 577 | 35210 | — | — | 61 |

Hence, as is shown by the experimental data presented above, the compounds of this invention uniquely effect the synthesis of the neurotransmitter dopamine and thus are useful in the treatment of dopaminergic disorders such as schizophrenia, Parkinson's Disease, Tourette's Syndrome, alcohol addiction, cocaine addiction, and addiction to analogous drugs.

Applicable solid carriers for pharmaceutical compositions containing the compounds of this invention can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis and the size, age and response pattern of the patient.

What is claimed is:

1. A compound of the formula:

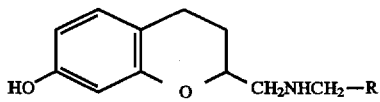

I in which

R is a straight or branched chain alkyl group of 1 to 6 carbon atoms, hydroxyalkyl of 1 to 6 carbon atoms or a cycloalkyl group of 3 to 8 carbon atoms;

or a pharmaceutically acceptable salt thereof.

2. The compound of claim 1 which is 2-(butylaminomethyl)-chroman-7-ol or a pharmaceutically acceptable salt thereof.

3. The compound of claim 1 which is 2-(propylaminomethyl)-chroman-7-ol or a pharmaceutically acceptable salt thereof.

4. The compound of claim 1 which is 2-(isobutylaminomethyl)-chroman-7-ol or a pharmaceutically acceptable salt thereof.

5. The compound of claim 1 which is 2-[(3-methylbutylamino)-methyl]-chroman-7-ol or a pharmaceutically acceptable salt thereof.

6. The compound of claim 1 which is 2-(pentylaminomethyl)-chroman-7-ol or a pharmaceutically acceptable salt thereof.

7. The compound of claim 1 which is 2-(hexylaminomethyl)-chroman-7-ol or a pharmaceutically acceptable salt thereof.

8. The compound of claim 1 which is 2-[(3-hydroxypropylamino)-methyl]-chroman-7-ol or a pharmaceutically acceptable salt thereof.

9. The compound of claim 1 which is 2-[(cyclohexylmethyl-amino)-methyl]-chroman-7-ol or a pharmaceutically acceptable salt thereof.

10. A pharmaceutical composition of matter comprising a compound of the formula:

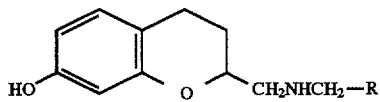

I in which

R is a straight or branched chain alkyl group of 1 to 6 carbon atoms, hydroxyalkyl of 1 to 6 carbon atoms or a cycloalkyl group of 3 to 8 carbon atoms;

or a pharmaceutically acceptable salt thereof and a pharmaceutically acceptable carrier therefor.

11. A method for reducing dopamine synthesis and release in a patient suffering from hyperactivity of the dopaminergic systems, which comprises administering to said patient a compound of the formula:

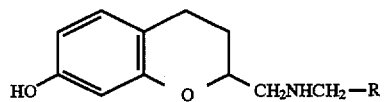

I in which

R is a straight or branched chain alkyl group of 1 to 6 carbon atoms, hydroxyalkyl of 1 to 6 carbon atoms or a cycloalkyl group of 3 to 8 carbon atoms;

or a pharmaceutically acceptable salt thereof, in an amount sufficient to modulate the dopamine systems of the brain.

12. A method for treating schizophrenia which comprises administering to a patient suffering from schizophrenia, orally or parenterally, a compound of the formula:

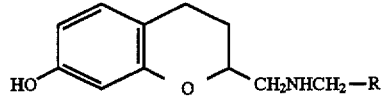

I in which

R is a straight or branched chain alkyl group of 1 to 6 carbon atoms, hydroxyalkyl of 1 to 6 carbon atoms or a cycloalkyl group of 3 to 8 carbon atoms;

or a pharmaceutically acceptable salt thereof, in an amount sufficient to alleviate the symptoms of schizophrenia.

* * * * *